United States Patent [19]

Blackwell

[11] Patent Number: 5,932,627
[45] Date of Patent: Aug. 3, 1999

[54] FLUORIDE RELEASING DENTAL PRIMER COMPOSITION AND METHOD

[75] Inventor: Gordon Blackwell, Constance, Germany

[73] Assignee: Dentsply GmbH, Germany

[21] Appl. No.: 08/879,511

[22] Filed: Jun. 20, 1997

Related U.S. Application Data

[63] Continuation of application No. 08/555,379, Nov. 9, 1995, abandoned, which is a continuation of application No. 08/241,909, May 12, 1994, abandoned.

[51] Int. Cl.$^6$ .............................. A61K 6/08; C08K 5/02
[52] U.S. Cl. ..................... 523/118; 524/236; 526/277; 526/301; 523/116; 433/228.1
[58] Field of Search .................... 523/118, 116; 524/236; 526/277, 301; 433/228.1

[56] References Cited

U.S. PATENT DOCUMENTS

| | | | |
|---|---|---|---|
| 2,980,733 | 4/1961 | Sowa | 260/555 |
| 3,341,505 | 9/1967 | Gander | 260/86.1 |
| 3,629,187 | 12/1971 | Waller | 260/41 |
| 3,709,866 | 1/1973 | Waller | 260/27 |
| 3,759,809 | 9/1973 | Carlick et al. | 204/159.23 |
| 3,881,026 | 4/1975 | Shepherd et al. | 424/487 |
| 3,882,600 | 5/1975 | Plymale | 32/15 |
| 3,914,406 | 10/1975 | Yankell | 424/52 |
| 3,969,499 | 7/1976 | Lee, Jr. et al. | 424/52 |
| 3,997,504 | 12/1976 | Plymale . | |
| 4,044,044 | 8/1977 | Saito | 260/47 |
| 4,071,424 | 1/1978 | Dart et al. | 204/159.15 |
| 4,089,763 | 5/1978 | Dart et al. | 204/159.23 |
| 4,107,845 | 8/1978 | Lee, Jr. et al. | 32/15 |
| 4,143,126 | 3/1979 | Gaffar | 424/49 |
| 4,150,116 | 4/1979 | Taubman et al. | 424/88 |

(List continued on next page.)

FOREIGN PATENT DOCUMENTS

| | | |
|---|---|---|
| 559648 | 7/1958 | Canada . |
| 940647 | 1/1974 | Canada . |
| 960226 | 12/1974 | Canada . |
| 978304 | 11/1975 | Canada . |
| 983190 | 2/1976 | Canada . |
| 1011489 | 5/1977 | Canada . |
| 1047670 | 1/1979 | Canada . |
| 1052032 | 4/1979 | Canada . |
| 1075067 | 4/1980 | Canada . |
| 1121548 | 4/1982 | Canada . |
| 1138149 | 12/1982 | Canada . |
| 1143085 | 3/1983 | Canada . |
| 1143086 | 3/1983 | Canada . |
| 1148294 | 6/1983 | Canada . |
| 1148832 | 6/1983 | Canada . |
| 1159595 | 12/1983 | Canada . |
| 1170186 | 7/1984 | Canada . |
| 1312402 | 7/1985 | Canada . |
| 1198444 | 12/1985 | Canada . |
| 1198847 | 12/1985 | Canada . |
| 1202441 | 3/1986 | Canada . |
| 1203484 | 4/1986 | Canada . |
| 1207944 | 7/1986 | Canada . |
| 1226395 | 9/1987 | Canada . |
| 1234241 | 3/1988 | Canada . |
| 1236844 | 5/1988 | Canada . |
| 1238141 | 6/1988 | Canada . |
| 1243796 | 10/1988 | Canada . |
| 1244581 | 11/1988 | Canada . |
| 1253289 | 4/1989 | Canada . |
| 1254336 | 5/1989 | Canada . |
| 1255030 | 5/1989 | Canada . |
| 1259149 | 9/1989 | Canada . |
| 1262796 | 11/1989 | Canada . |
| 2026203 | 4/1990 | Canada . |
| 2014856 | 10/1990 | Canada . |
| 2015922 | 11/1990 | Canada . |
| 2034498 | 12/1990 | Canada . |
| 2026417 | 9/1991 | Canada . |
| 1308216 | 9/1992 | Canada . |
| 2088633 | 8/1993 | Canada . |
| 26539 | 4/1981 | European Pat. Off. . |
| 088527 A3 | 9/1983 | European Pat. Off. . |
| 183027 A2 | 6/1986 | European Pat. Off. . |
| 0 237 233 | 9/1987 | European Pat. Off. . |
| 363903 A2 | 4/1990 | European Pat. Off. . |
| 396459 A1 | 7/1990 | European Pat. Off. . |
| 499 180 | 8/1992 | European Pat. Off. . |
| 2 606 022 | 11/1987 | France . |
| 2925020 | 1/1981 | Germany . |
| 63-255209 A2 | 10/1988 | Japan . |
| 9015591 A1 | 6/1990 | WIPO . |

OTHER PUBLICATIONS

Shern et al; Journal of Oral Medicine; Jul.–Sep. 1970; pp. 95–97; Prevention Of Plaque Formation By Organic Fluorides.

Lexis Search A—Dental and Fluoride: Appendix A Dental an Cetylameine Hydrofluoride: Appendix B Coltene: Appendix C.

Lexis Search B—Dental, Quaternary and Fluoride Coltene Whaledent.

Coltene Whaledent A.R.T. Bond, Advanced Retention Technology (2 pages) (Mar. 1988).

*Primary Examiner*—Andrew E. C. Merriam
*Attorney, Agent, or Firm*—Dale R. Lovercheck; James B. Bieber

[57] ABSTRACT

The invention provides a fluoride releasing dental primer composition which includes a polymerizable acrylic compound, a light activated catalyst, and an organic amino hydrofluoride. This fluoride releasing dental primer composition is used by applying it to dentin and illuminating it with visible light to polymerize the polymerizable acrylic compound. The invention provides a method of priming dentin by applying a fluoride releasing dental primer composition. The fluoride releasing dental primer composition has a polymerizable acrylic compound, a light activated catalyst, and an organic amino hydrofluoride having from about 2 to about 30 carbon atoms. The polymerizable acrylic compound is adapted to polymerize to form polymeric material. The organic amino hydrofluoride is adapted to leach from the polymeric material, chelate to dentin and release fluoride.

37 Claims, No Drawings

U.S. PATENT DOCUMENTS

| | | | |
|---|---|---|---|
| 4,182,035 | 1/1980 | Yamauchi et al. | 433/228 |
| 4,189,365 | 2/1980 | Schmitt et al. | 204/159.23 |
| 4,222,780 | 9/1980 | Shibatani et al. | 106/35 |
| 4,224,023 | 9/1980 | Cheung | 433/216 |
| 4,235,633 | 11/1980 | Tomioka et al. | 106/35 |
| 4,250,262 | 2/1981 | Taubman et al. | 435/193 |
| 4,259,117 | 3/1981 | Yamauchi et al. | 106/35 |
| 4,291,097 | 9/1981 | Kamada et al. | 428/412 |
| 4,292,029 | 9/1981 | Craig et al. | 433/228 |
| 4,308,014 | 12/1981 | Kawahara et al. | 433/228 |
| 4,327,014 | 4/1982 | Kawahara et al. | 523/116 |
| 4,335,102 | 6/1982 | Nakashima et al. | 424/52 |
| 4,351,881 | 9/1982 | Kamada et al. | 428/412 |
| 4,363,794 | 12/1982 | Ochiai et al. | 424/52 |
| 4,368,043 | 1/1983 | Yamauchi et al. | 433/217 |
| 4,374,937 | 2/1983 | Nemcek et al. | 523/116 |
| 4,376,673 | 3/1983 | Cheung | 156/662 |
| 4,396,377 | 8/1983 | Roemer et al. | 433/199 |
| 4,396,476 | 8/1983 | Roemer et al. | 204/159.16 |
| 4,411,625 | 10/1983 | Koblitz et al. | 433/217 |
| 4,426,404 | 1/1984 | Shoher et al. | 427/2 |
| 4,433,124 | 2/1984 | Okamoto et al. | 526/28 |
| 4,439,554 | 3/1984 | Argentar | 523/115 |
| 4,440,878 | 4/1984 | Kawahara et al. | 523/116 |
| 4,455,293 | 6/1984 | Harvey et al. | 424/52 |
| 4,455,294 | 6/1984 | Harvey et al. | 424/52 |
| 4,457,818 | 7/1984 | Denyer et al. | 204/159.19 |
| 4,459,193 | 7/1984 | Ratcliffe et al. | 204/159.23 |
| 4,469,674 | 9/1984 | Shah et al. | 424/52 |
| 4,491,453 | 1/1985 | Koblitz et al . | 433/217 |
| 4,499,251 | 2/1985 | Omura et al. | 526/278 |
| 4,512,743 | 4/1985 | Santucci et al. | 433/217 |
| 4,514,342 | 4/1985 | Billington et al. | 260/952 |
| 4,515,910 | 5/1985 | Rawls et al. | 523/115 |
| 4,526,778 | 7/1985 | Harvey et al. | 424/52 |
| 4,539,382 | 9/1985 | Omura et al. | 526/276 |
| 4,540,722 | 9/1985 | Bunker | 523/109 |
| 4,572,920 | 2/1986 | Rawls et al. | 523/115 |
| 4,612,384 | 9/1986 | Omura et al. | 558/198 |
| 4,626,310 | 12/1986 | Ritter | 156/307.3 |
| 4,650,847 | 3/1987 | Omura et al. | 526/376 |
| 4,657,941 | 4/1987 | Blackwell et al. | 522/14 |
| 4,669,983 | 6/1987 | Bunker | 433/217.1 |
| 4,670,576 | 6/1987 | Bunker | 558/182 |
| 4,673,354 | 6/1987 | Culler | 433/217.1 |
| 4,675,358 | 6/1987 | Frangou | 524/439 |
| 4,685,969 | 8/1987 | Schmid et al. | 106/35 |
| 4,693,888 | 9/1987 | Miyahara et al. | 424/49 |
| 4,698,373 | 10/1987 | Tateosian et al. | 522/95 |
| 4,702,904 | 10/1987 | Maeyama et al. | 424/52 |
| 4,719,149 | 1/1988 | Aasen et al. | 428/473 |
| 4,725,428 | 2/1988 | Miyahara et al. | 424/50 |
| 4,760,122 | 7/1988 | Nakos et al. | 526/242 |
| 4,767,614 | 8/1988 | Scarpa et al. | 424/48 |
| 4,771,112 | 9/1988 | Engelbrecht | 525/327.3 |
| 4,772,325 | 9/1988 | Kwan et al. | 106/35 |
| 4,814,423 | 3/1989 | Huang et al. | 528/230 |
| 4,816,495 | 3/1989 | Blackwell et al. | 522/14 |
| 4,820,545 | 4/1989 | Negrych | 427/2 |
| 4,828,822 | 5/1989 | Muhlemann et al. | 424/52 |
| 4,855,475 | 8/1989 | Bunker | 558/182 |
| 4,867,988 | 9/1989 | Chernack | 424/490 |
| 4,871,786 | 10/1989 | Aasen et al. | 523/113 |
| 4,880,660 | 11/1989 | Aasen et al. | 427/2 |
| 4,911,918 | 3/1990 | Kiyoshige et al. | 424/50 |
| 4,966,934 | 10/1990 | Huange et al. | 524/315 |
| 4,968,725 | 11/1990 | Mukai et al. | 522/90 |
| 5,009,593 | 4/1991 | Vogelstein | 433/221 |
| 5,011,691 | 4/1991 | Oppermann et al. | 424/423 |
| 5,037,638 | 8/1991 | Hamer et al. | 424/52 |
| 5,049,504 | 9/1991 | Maugh et al. | 435/252.33 |
| 5,073,112 | 12/1991 | Weil | 433/221 |
| 5,084,491 | 1/1992 | Kerby | 523/116 |
| 5,098,304 | 3/1992 | Scharf | 433/215 |
| 5,098,997 | 3/1992 | Anilionis et al. | 530/350 |
| 5,104,591 | 4/1992 | Masuhara et al. | 264/16 |
| 5,110,633 | 5/1992 | Casset et al. | 427/430.1 |
| 5,112,880 | 5/1992 | Tsunekawa et al. | 522/81 |
| 5,174,989 | 12/1992 | Tanaka et al. | 424/52 |
| 5,189,077 | 2/1993 | Kerby | 523/116 |
| 5,196,338 | 3/1993 | Anilionis et al. | 435/252.3 |
| 5,202,236 | 4/1993 | Maugh et al. | 435/69.1 |
| 5,202,256 | 4/1993 | Maugh et al. | 435/252.3 |
| 5,202,422 | 4/1993 | Hiatt et al. | 530/387.3 |
| 5,218,070 | 6/1993 | Blackwell | 526/318 |

FLUORIDE RELEASING DENTAL PRIMER COMPOSITION AND METHOD

This is a continuation of application Ser. No. 08/555,379, filed Nov. 9, 1995 now abandoned which is a continuation of application Ser. No. 08/241,909 filed May 12, 1994, now abandoned.

The invention relates to dental compositions which release fluoride. The invention provides a fluoride releasing dental primer composition and method of use thereof.

Plymale in U.S. Pat. No. 3,997,504 discloses composition and method for treating teeth. Rawls et al in U.S. Pat. No. 4,515,910 discloses interpolymeric resin for treatment of teeth. Rawls et al in U.S. Pat. No. 4,572,920 discloses fluoride interpolymeric resin. Aasen et al in U.S. Pat. No. 4,871,786 discloses organic fluoride sources. Hamer et al in U.S. Pat. No. 5,037,638 discloses fluoride release agent copolymer prepared using morpholinoethyl methacrylate hydrofluoride comonmer. Tsunekawa et al in U.S. Pat. No. 5,112,880 discloses light-curable orthodontic bracket adhesive. Tanada et al in U.S. Pat. No. 5,174,989 discloses oral composition. Blackwell in U.S. Pat. No. 5,218,070 discloses dental/medical composition and use.

The prior art does not provide a fluoride releasing dental primer composition which includes a polymerizable acrylic compound, a light activated catalyst, and an organic amino hydrofluoride as is provided by the present invention.

It is an object of the invention to provide a fluoride releasing dental primer composition which includes a polymerizable acrylic compound, a light activated catalyst, and an organic amino hydrofluoride.

It is an object of the invention to provide a method of priming dentin which includes applying to dentin a fluoride releasing dental primer composition containing a polymerizable acrylic compound, a light activated catalyst, and an organic amino hydrofluoride.

"Monomer" as used herein refers to monomer and/or oligomer.

BRIEF SUMMARY OF THE INVENTION

The invention provides a fluoride releasing dental primer composition which includes a polymerizable acrylic compound, a light activated catalyst, and an organic amino hydrofluoride. This fluoride releasing dental primer composition is used by applying it to dentin and illuminating it with visible light to polymerize the polymerizable acrylic compound. The invention provides a method of priming dentin by applying a fluoride releasing dental primer composition. The fluoride releasing dental primer composition has a polymerizable acrylic compound, a light activated catalyst, and an organic amino hydrofluoride having from about 2 to about 30 carbon atoms. The polymerizable acrylic compound is adapted to polymerize to form polymeric material. The organic amino hydrofluoride is adapted to leach from the polymeric material, chelate to dentin and release fluoride.

DETAILED DESCRIPTION OF THE INVENTION

In accordance with a preferred embodiment of the invention is provided a fluoride releasing dental primer composition which includes a polymerizable acrylic compound, a catalyst, and an organic amino hydrofluoride. The polymerizable acrylic compound is adapted to polymerize to form polymeric material. The organic amino hydrofluoride is adapted to leach from the polymeric material, chelate to dentin and release fluoride. The fluoride releasing primer composition is applied to dentin of a tooth in the mouth (oral cavity) of a patient. Preferably the patient is a human being. This fluoride releasing primer composition is brushed as a thin coating onto a prepared dentin surfaced, and cured for ten seconds by exposure to visible light before applying a composite. The primer coating on the dentin bonds thereto with an adhesion preferably of at least 9 MPa. A preferred fluoride releasing dental primer composition includes a polymerizable acrylic compound, a light activated catalyst, and an organic amino hydrofluoride. Preferably, the organic amino hydrofluoride is an alkyl amino hydrofluoride having from about 2 to about 30 carbon atoms.

Preferably the concentration of organic amine fluoride is from about 0.1 to about 5 percent by weight of the primer composition, and is completely soluble in the resin. Accordingly, the primer composition is shelf stable and does not separate during storage. Thus, no mixing or shaking of the primer is needed before use. When the fluoride leaches out of the cured resin, no voids are left. This provides better aesthetics and a reduced possibility of staining than prior art compositions. The adhesive layer formed is continuous and does not include solid particles which potentially interfere with adhesion.

The amines useful in accordance with the invention preferably chelate to the dentin and/or enamel, thereby preventing bacteria from adhering and causing decay. Chelaton to dentin and/or enamel does not occur in prior art primers which include inorganic fluorides, such as sodium fluoride. Cetylamine hydrofluoride is a preferred organic amine hydrofluoride for use in the composition of the invention as it has no adverse effect on the properties of the primer.

The six months data in Table 2 relates to adhesion using a primer solution which has been stored at room temperature for six months before use. The amine does not separate from primer composition in accordance with the invention stored at 4° C.

The fluoride releasing dental primer composition of the invention preferably releases at least 0.1 $\mu$g of fluoride per square cm per week measured using a selective fluoride ion electrode in 10% TISAB IV buffer. TISAB IV buffer is made by stirring together sodium chloride (58 g), ethylenediaminetetracarboxylic acid (EDTA, 5 g), and distilled water (500 ml), and adding just enough 32% sodium hydroxide solution to cause complete dissolution of the EDTA, glacial acetic acid (57 ml) is then added, followed by enough 32% sodium hydroxide solution to raise the pH of the mixture to between 5 and 5.5.

The invention is now described in the following specific examples. The procedure of Example 1, part A is in accordance with U.S. Pat. No. 4,814,423 assigned to Dentsply Research and Development Corporation.

EXAMPLE 1

A) To a mechanically-stirred mixture of 28.59 weight parts of trimethylhexamethylene diisocyanate and 0.04 weight part of stannous octoate in a reactor and purged with dry air, there is added 44.80 weight parts of polytetramethylene ether glycol, while maintaining the reaction temperature at 50° to 60° C. After the addition is complete, the mixture is heated to 70° to 80° C. and held for 3 hours. A 26.58 weight parts of hydroxyethyl methacrylate (HEMA) is added and the mixture is stirred at 70° to 80° C. until the percent NCO assay is below 0.01%.

B) 5 g of dipentaerythritol pentaacrylate phosphoric acid ester (PENTA), 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.2 g of cetylamine hydrofluoride, and 79.0 g of acetone are mixed to form a dental primer composition. The dental primer composition is applied to dentin and illuminated with visible light for ten seconds to form a primer coating. The strength of adhesion of this primer coating to dentin and fluoride released from the primer coating are shown in Table 1.

EXAMPLE 2

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.1 g of cetylamine hydrofluoride, and 79.1 g of acetone are mixed to form a dental primer composition. The dental primer composition is applied to dentin and illuminated with visible light for ten seconds to form a primer coating. The strength of adhesion of this primer coating to dentin and fluoride released from the primer coating are shown in Table 1.

EXAMPLE 3

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.02 g of cetylamine hydrofluoride, and 79.18 g of Acetone are mixed to form a dental primer composition. The dental primer composition is applied to dentin and illuminated with visible light for ten seconds to form a primer coating. The strength of adhesion of this primer coating to dentin and fluoride released from the primer coating are shown in Table 1.

TABLE 1

Fluoride releasing primer formulations, adhesion and fluoride release

| | Percent by weight | | |
|---|---|---|---|
| Example | 1 | 2 | 3 |
| PENTA | 5.0 | 5.0 | 5.0 |
| Triethylenenglycol dimethacrylate | 5.0 | 5.0 | 5.0 |
| urethane diacrylate Monomer | 10.0 | 10.0 | 10.0 |
| Camphorquinone | 0.2 | 0.2 | 0.2 |
| 4-Dimethylaminoethyl benzoate (DMABE) | 0.6 | 0.6 | 0.6 |
| Cetylamine hydrofluoride | 0.2 | 0.1 | 0.02 |
| Acetone | 79.0 | 79.1 | 79.18 |
| Adhesion to dentin (MPa) | | | |
| Using fresh primer samples stored 24 hours at 37° C. samples thermocycled | 11.6 (2) | 16.3 (2.0) | 13.2 (2.7) |
| Fluoride release per week (µg F-) | | | |
| Weeks | | | |
| 1 | 62.5 | 23.8 | 6.0 |
| 2 | 8.7 | 1.8 | 0.4 |
| 3 | 1.7 | 0.1 | 0.1 |
| 4 | 0.6 | 0.1 | 0.1 |
| 5 | 0.3 | 0.1 | 0.1 |
| 6 | 0.2 | 0.1 | 0.1 |
| 7 | 0.2 | 0.1 | 0.1 |
| 9 | 0.1 | 0.1 | 0.1 |

TABLE 1-continued

Fluoride releasing primer formulations, adhesion and fluoride release

| | Percent by weight | | |
|---|---|---|---|
| Example | 1 | 2 | 3 |
| 11 | 0.1 | 0.1 | 0.1 |
| 15 | 0.1 | 0.1 | 0.1 |

EXAMPLE 4

2.5 g of PENTA, 2.5 g of triethylenenglycol dimethacrylate, 5 g of the urethane dimethacrylate Monomer prepared as described in Example 1, part A, 0.02 g of camphorquinone, 0.06 g of 4-dimethylaminoethyl benzoate (DMABE), 0.005 g of BHT and 0.3 g of a 33 percent solution of bis(hydroxethyl)-aminopropyl-N-hydroxyethyl-octadecylamine dihydrofluoride in propanediol are mixed to form a dental primer composition. The dental primer composition is shaped in molds and illuminated with visible light for forty seconds to form cylindrical samples which are 4 mm in diameter and 6 mm in length. The elastic modulus is shown in Table 2.

EXAMPLE 5

2.5 g of PENTA, 2.5 g of triethylenenglycol dimethacrylate, 5 g of the urethane dimethacrylate Monomer prepared as described in Example 1, part A, 0.02 g of camphorquinone, 0.06 g of 4-dimethylaminoethyl benzoate (DMABE), 0.005 g of BHT, and 0.6 g of a 33 percent solution of bis(hydroxethyl)-aminopropyl-N-hydroxyethyl-octadecylamine dihydrofluoride in propanedial dental primer composition. The dental primer composition is shaped in molds and illuminated with visible light for forty seconds to form cylindrical samples which are 4 mm in diameter and 6 mm in length. The elastic modulus is shown in Table 2.

EXAMPLE 6

1.0 g of PENTA, 1.0 g of triethylenenglycol dimethacrylate, 2.0 g of the urethane dimethacrylate Monomer prepared as described in Example 1, part A, 0.04 g of camphorquinone, 0.12 g of 4-dimethylaminoethyl benzoate (DMABE), 0.01 g of BHT, 0.12 g of a 33 percent solution of bis(hydroxethyl)-aminopropyl-N-hydroxyethyl-octadecylamine dihydrofluoride in propanediol and 15.84 g of acetone are mixed to form a dental primer composition. The dental primer composition is applied to dentin and illuminated with visible light for ten seconds to form a primer coating. The strength of adhesion of this primer coating to dentin is shown in Table 2.

EXAMPLE 7

1.0 g of PENTA, 1.0 g of triethylenenglycol dimethacrylate, 2.0 g of the urethane dimethacrylate Monomer prepared as described in Example 1, part A, 0.04 g of camphorquinone, 0.12 g of 4-dimethylaminoethyl benzoate (DMABE), 0.01 g of BHT, and 0.24 g of a 33 percent solution of bis(hydroxethyl)-aminopropyl-N-hydroxyethyl-octadecylamine dihydrofluoride in propandiol and 15.84 g of acetone are mixed to form a dental primer composition. The dental primer composition is applied to dentin and illuminated with visible light for ten seconds to form a primer coating. The strength of adhesion of this primer coating to dentin is shown in Table 2.

EXAMPLE 8

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), and 0.5 g of cetylamine hydrofluoride are mixed to form a dental primer composition. The dental primer composition was shaped in molds 4 mm diameter and 6 mm long and illuminated with visible light for forty seconds to form cylindrical samples. The elastic modulus is shown in Table 2.

EXAMPLE 9

24.5 g of PENTA, 24.5 g of triethylenenglycol dimethacrylate, 49.05 g of the urethane dimethacrylate Monomer prepared as described in Example 1, part A, 0.2 g of camphorquinone, 0.6 g of 4-dimethylaminoethyl benzoate (DMABE), and 1 g of cetylamine hydrofluoride are mixed to form a dental primer composition. The dental primer composition is shaped in molds and illuminated with visible light for forty seconds to form rods which are 4 mm in diameter and 6 mm in length, the rods having an elastic modulus of 568.7 as shown in Table 2.

EXAMPLE 10

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.1 g of cetylamine hydrofluoride and 79.1 g of acetone are mixed to form a dental primer composition. The dental primer composition is applied to dentin and illuminated with visible light for ten seconds to form a primer coating. The adhesion to dentin is shown in Table 2.

EXAMPLE 11

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.5 g of cetylamine hydrofluoride and 78.1 g of acetone are mixed to form a dental primer composition. The dental primer composition is applied to dentin and illuminated with visible light for ten seconds to form a primer coating. The strength of adhesion of this primer coating to dentin is shown in Table 2.

EXAMPLE 12

1.5 g of PENTA, 1.5 g of triethylenenglycol dimethacrylate, 3 g of the urethane dimethacrylate Monomer prepared as described in Example 1, part A, 0.06 g of camphorquinone, 0.18 g of 4-dimethylaminoethyl benzoate (DMABE), 0.3 g of cetylamine hydrofluoride and 23.5 g of acetone are mixed to form a dental primer composition. The dental primer composition is applied to dentin and illuminated with visible light for ten seconds to form a primer coating. The strength of adhesion of this primer coating to dentin and is shown in Table 2.

EXAMPLE 13

10 g of dental primer composition prepared by following the procedure of Example 11 is stored for six months at 23° C. The dental primer composition is applied to dentin and illuminated with visible light for ten seconds to form a primer coating. The strength of adhesion of this primer coating to dentin is shown in Table 2.

EXAMPLE 14

Amine-free Comparative Composition 2.45 g of PENTA, 2.45 g of triethylenenglycol dimethacrylate, 4.9 g of the urethane dimethacrylate Monomer prepared as described in Example 1, part A, 0.02 g of camphorquinone, and 0.06 g of 4-dimethylaminoethyl benzoate (DMABE) are mixed to form a dental primer composition. The dental primer composition was shaped in molds to form rods 4 mm in diameter and 5 mm long and illuminated with visible light for forty seconds to form cylindrical samples. The elastic modulus are shown in Table 2.

EXAMPLE 15

Amine-free Comparative Composition 5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE) and 79.2 g of acetone are mixed to form a dental primer composition. The dental primer composition is applied to dentin and illuminated with visible light for ten seconds to form a primer coating. The strength of adhesion of this primer coating to dentin is shown in Table 2.

EXAMPLE 16

2.5 g of PENTA, 2.5 g of triethylenenglycol dimethacrylate, 5 g of the urethane dimethacrylate Monomer prepared as described in Example 1, part A, 0.2 g of camphorquinone, 0.6 g of 4-dimethylaminoethyl benzoate (DMABE), and 0.01 g of ammonium fluoride are mixed to form a dental primer composition. The dental primer composition is shaped in molds to form rods 4 mm diameter and 6 mm long and illuminated with visible light for forty seconds to form cylindrical samples. The elastic modulus is shown in Table 2.

EXAMPLE 17

2.4 g of PENTA, 2.4 g of triethylenenglycol dimethacrylate, 4.8 g of the urethane dimethacrylate Monomer prepared as described in Example 1, part A, 0.96 g of camphorquinone, 0.29 g of 4-dimethylaminoethyl benzoate (DMABE), 0.01 g of ammonium fluoride and 38.0 g of Acetone are mixed to form a dental primer composition. The dental primer composition is applied to dentin and illuminated with visible light for ten seconds to form a primer coating. The strength of adhesion of this primer coating to dentin is shown in Table 2.

EXAMPLE 18

5 g of PENTA, 5 g of triethylenenglycol dimethacrylate, 10 g of the urethane dimethacrylate Monomer prepared as described in Example 1, part A, 0.2 g of camphorquinone, 0.6 g of 4-dimethylaminoethyl benzoate (DMABE), 0.2 g of ammonium fluoride and 79.2 g of acetone are mixed to form a dental primer composition. The dental primer composition is applied to dentin and illuminated with visible light for ten seconds to form a primer coating. The adhesion to dentin is shown in Table 2.

TABLE 2

| Examples 4–18 | Amine type | Amine % in resin part | Elastic modulus | Adhesion to dentin thermo-cycled MPa |
|---|---|---|---|---|
| 4 | BEAP | 1.0 | 454.40 | |
| 5 | BEAP | 2.0 | 360.20 | |
| 6 | BEAP | 1.0 | | 15.3 ± 2.1 |
| 7 | BEAP | 2.0 | | 13.0 ± 2.6 |
| 8 | CAF | 0.5 | 662.6 | |
| 9 | CAF | 1.0 | 568.70 | |
| 10 | CAF | 0.1 | | 10.9 ± 3.0 |
| 11 | CAF | 0.5 | | 10.5 ± 3.8 |
| 12 | CAF | 1.0 | | 13.0 ± 5.2 |
| 13 | CAF | 0.5 | | 15.8 ± 2.1 |
| six months old | | | | |
| 14 | NONE | 0.0 | 611.80 | |
| 15 | NONE | 0.0 | | 14.5 ± 2.1 |
| 16 | NHF | 0.1 | 631.30 | |
| 17 | NHF | 0.1 | | 14.9 ± 3.6 |
| 18 | NHF | 0.2 | | 12.8 ± 3.2 |

The amines used in Examples 4–18 are cetylamine hydrofluoride (CAF), a 30% solution of bis(hydroxethyl)-aminopropyl-N-hydroxyethyl-octadecylamine dihydrofluoride in propylenediol (BEAP) and ammonium fluoride (NHF).

In Table 3 are shown the adhesion to dentin and cumulative fluoride release in $\mu$g for the products of Examples 1, 3, 4, 5, 11 and 16.

TABLE 3

| Example | 1 | 11 | 3 | 17 | 6 | 7 |
|---|---|---|---|---|---|---|
| Adhesion to dentin after thermocycling (and standard deviation) | 13.1<br>5.2 | 10.5<br>3.8 | 10.9<br>3.0 | 14.9<br>3.6 | 15.3<br>2.1 | 13.0<br>2.6 |
| Cumulative fluoride ($\mu$g) release in weeks | | | | | | |
| 1 | 62.5 | 23.8 | 6.0 | 21.1 | 57.7 | 70.4 |
| 2 | 71.2 | 25.6 | 6.4 | 22.2 | 63.1 | 74.9 |
| 3 | 72.9 | 25.7 | 6.5 | 22.4 | 63.6 | |
| 4 | 73.5 | 25.8 | 6.6 | 22.5 | | |
| 5 | 73.8 | 25.9 | 6.7 | | | |
| 6 | 74.0 | 26.0 | 6.8 | | | |
| 7 | 74.2 | 26.1 | 6.9 | | | |
| 8 | 74.3 | 26.2 | 7.0 | | | |
| 9 | 74.4 | 26.3 | 7.1 | | | |
| 10 | 74.5 | 26.4 | 7.2 | | | |

It should be understood that while the present invention has been described in considerable detail with respect to certain specific embodiments thereof, it should not be considered limited to such embodiments but may be used in other ways without departure from the spirit of the invention and the scope of the appended claims.

I claim:

1. A fluoride releasing liquid dental primer product formed by providing a composition, comprising:
   a polymerizable acrylic compound,
   a catalyst,
   an alkyl amino hydrofluoride, and
   volatile solvent, said volatile solvent comprising at least 50 percent by weight of said composition,
   applying said composition to dentin,
   polymerizing said polymerizable acrylic compound to form polymeric material,
   said alkyl amino hydrofluoride being effectively completely soluble in said polymerizable acrylic compound.

2. The product of claim 1 wherein said polymeric material has an adhesion to said dentin of at least 9 MPa and said release of fluoride at a rate of at least 0.1 $\mu$g of fluoride per week is for at least four weeks.

3. The product of claim 1 wherein said alkyl amino hydrofluoride is cetylamine hydrofluoride.

4. The product of claim 3 wherein said catalyst is camphorquinone and said polymerizable acrylic compound is triethyleneglycol dimethacrylate.

5. The product of claim 1 wherein said polymerizable acrylic compound is dipentaerythritol pentaacrylate phosphoric acid ester.

6. The product of claim 1 wherein said polymeric material has an adhesion to said dentin of at least 9 MPa.

7. The composition of claim 1 wherein said alkyl amino hydrofluoride leaching from said polymeric material and chelating to dentin effectively prevents bacteria from adhering and causing decay, and within two weeks of said forming said polymeric material said alkyl amino hydrofluoride releases fluoride at a substantially constant rate of at least 0.1 $\mu$g of fluoride per week for at least three weeks.

8. The product of claim 6 wherein said polymeric material is a polymeric primer coating adapted to release fluoride at a rate of at least 0.1 $\mu$g of fluoride per week for at least nine weeks.

9. The product of claim 6 wherein said polymeric material is adapted to release at least 0.1 mg of fluoride per week.

10. The product of claim 7 wherein said polymerizable acrylic compound is a urethane dimethacrylate.

11. The product of claim 1 wherein said catalyst is a light activated catalyst.

12. The product of claim 1 wherein said alkyl amino hydrofluoride has from about 2 to about 30 carbon atoms.

13. The product of claim 1 wherein within two weeks of said forming said polymeric material said alkyl amino hydrofluoride releases fluoride at a substantially constant rate of at least 0.1 mg of fluoride per week and said release of fluoride is for at least three weeks.

14. The product of claim 13 wherein said release of fluoride is for at least six weeks.

15. The product of claim 13 wherein said release of fluoride is for at least nine weeks.

16. The product of claim 13 wherein said release of fluoride is for at least fifteen weeks.

17. The product of claim 13 wherein said rate is at least 0.4 $\mu$g of fluoride per week.

18. A method of priming dentin, comprising;
   providing a fluoride releasing liquid dental primer composition, comprising:
   a polymerizable acrylic compound,
   a light activated catalyst,
   an alkyl amino hydrofluoride having from about 2 to about 30 carbon atoms, and
   a volatile solvent, said volatile solvent comprising at least 50 percent by weight of said composition,
   applying said composition to dentin and
   polymerizing said polymerizable acrylic compound to form a coating of polymeric material having an adhesion to said dentin of at least 9 MPa,
   said alkyl amino hydrofluoride being effectively completely soluble in said polymerizable acrylic compound.

19. The method of claim 18 wherein said alkyl amino hydrofluoride is adapted to leach from said polymeric material, chelate to said dentin, effectively prevents bacteria from adhering and causing decay, and within nine weeks of forming said polymeric material said alkyl amino hydrofluoride releases fluoride at a substantially constant rate of at least 0.1 μg of fluoride per week for at least two weeks.

20. The method of claim 18 wherein said volatile solvent is acetone.

21. The method of claim 18 wherein said alkyl amino hydrofluoride is cetylamine hydrofluoride.

22. The method of claim 18 wherein said catalyst is camphorquinone and said polymerizable acrylic compound is triethyleneglycol dimethacrylate.

23. The method of claim 18 wherein said polymerizable acrylic compound is dipentaerythritol pentaacrylate phosphoric acid ester.

24. The method of claim 18 wherein said composition is polymerized on dentin to form a polymeric coating with an adhesion to said dentin of at least 9 MPa, and said release of fluoride is at a rate of at least 0.1 μg of fluoride per week for at least three weeks.

25. The method of claim 24 wherein said polymeric primer coating is adapted to release a portion of said fluoride.

26. The method of claim 24 wherein said polymeric primer coating is adapted to release at least 0.1 g of fluoride per week.

27. The method of claim 23 wherein said alkyl amino hydrofluoride has from 2 to 30 carbon atoms.

28. The method of claim 18 wherein said catalyst is a light activated catalyst.

29. The method of claim 18 wherein said alkyl amino hydrofluoride is free of any polymerizable acrylate or acrylate moiety.

30. The method of claim 18 wherein said polymerization is initiated by illuminating said dental priming composition with visible light.

31. A fluoride releasing liquid dental primer composition, comprising:

a polymerizable acrylic compound, a catalyst, an alkyl amino hydrofluoride, and acetone, said acetone comprising at least 50 percent by weight of said composition, said polymerizable acrylic compound being adapted to polymerize to form polymeric material, said alkyl amino hydrofluoride being effectively completely soluble in said polymerizable acrylic compound.

32. The composition of claim 30 wherein said alkyl amino hydrofluoride is adapted to leach from said polymeric material, chelate to dentin preventing bacteria from adhering and causing decay, and within three weeks of forming said polymeric material said alkyl amino hydrofluoride being adapted to release fluoride at a substantially constant rate of at least 0.1 μg of fluoride per week for at least two weeks.

33. The composition of claim 32 wherein said release of fluoride is for at least nine weeks and said rate is at least 0.4 μg of fluoride per week.

34. A fluoride releasing liquid dental primer composition, comprising:

a polymerizable acrylic compound, a catalyst, a dentin chelate forming fluoride containing compound, and volatile solvent, said volatile solvent comprising at least 50 percent by weight of said composition, said polymerizable acrylic compound being adapted to polymerize to form polymeric material, said dentin chelate forming fluoride containing compound being effectively completely soluble in said polymerizable acrylic compound.

35. The composition of claim 33 wherein said dentin chelate forming fluoride containing compound is adapted to leach from said polymeric material, chelate to dentin effectively preventing bacteria from adhering and causing decay, and within two weeks of forming said polymeric material said dentin chelate forming fluoride containing compound being adapted to release fluoride at a substantially constant rate of at least 0.1 μg of fluoride per week for at least four weeks.

36. A method of priming and chelating dentin, comprising;

applying to dentin a fluoride releasing liquid dental priming and chelating composition, comprising:

a polymerizable acrylic compound, a light activated catalyst, a dentin chelate forming fluoride containing compound having from about 2 to about 30 carbon atoms, and a volatile solvent, said volatile solvent comprising at least 50 percent by weight of said composition, and polymerizing said polymerizable acrylic compound to form a coating of polymeric material having an adhesion to said dentin of at least 9 MPa, said dentin chelate forming fluoride containing compound being effectively completely soluble in said polymerizable acrylic compound.

37. The method of claim 36 wherein said dentin chelate forming fluoride containing compound leaching from said polymeric material, and chelating to said dentin to effectively prevents bacteria from adhering and causing decay, and said dentin chelate forming fluoride containing compound being adapted to release fluoride at a substantially constant rate of at least 0.1 μg of fluoride per week for at least four weeks.

* * * * *